(12) United States Patent  
Wiseman et al.

(10) Patent No.: US 8,203,117 B2
(45) Date of Patent: Jun. 19, 2012

(54) METHOD AND APPARATUS FOR EMBEDDED HEATER FOR DESORPTION AND IONIZATION OF ANALYTES

(75) Inventors: Justin M. Wiseman, Zionsville, IN (US); Brian C. Laughlin, Brownsburg, IN (US)

(73) Assignee: Prosolia, Inc., Indianapolis, IN (US)

( * ) Notice: Subject to any disclaimer, the term of this patent is extended or adjusted under 35 U.S.C. 154(b) by 319 days.

(21) Appl. No.: 12/568,929

(22) Filed: Sep. 29, 2009

(65) Prior Publication Data

US 2010/0078550 A1  Apr. 1, 2010

Related U.S. Application Data

(60) Provisional application No. 61/194,770, filed on Sep. 30, 2008.

(51) Int. Cl.
*H01J 49/04* (2006.01)
(52) U.S. Cl. ...................................... 250/288
(58) Field of Classification Search .................. 250/288, 250/281, 282
See application file for complete search history.

(56) References Cited

U.S. PATENT DOCUMENTS

| 4,814,612 | A | 3/1989 | Vestal et al. |
| 7,145,136 | B2 | 12/2006 | Yang et al. |
| 7,193,223 | B2 | 3/2007 | Franzen |
| 7,335,897 | B2 | 2/2008 | Takats et al. |
| 7,462,824 | B2 * | 12/2008 | Wang .......................... 250/288 |
| 7,847,244 | B2 * | 12/2010 | Venter et al. ............... 250/288 |

FOREIGN PATENT DOCUMENTS

| WO | WO2005/094389 | 10/2005 |
| WO | WO2007/138371 | 12/2007 |
| WO | WO2008/082603 | 7/2008 |
| WO | PCT/US2009/058717 | 11/2009 |

OTHER PUBLICATIONS

Cooks et al. 2006 Science 311: 1566-1570.
Takats et al. 2004 Science 306: 471-473.
Venter et al. 2008 Abstract from 56th ASMS Annu Conf Denver CO.

* cited by examiner

*Primary Examiner* — Kiet T Nguyen
(74) *Attorney, Agent, or Firm* — Michael Falkoff; Sonia K. Guterman; Sanjeev K. Mahanta (57) ABSTRACT

A heated DESI spray device provides improved resolution or control of analyte desorption at a target locus on a sample. Heating controls spot size and enhances resolution in an imaging mode without impairing signal level. Additionally or alternatively the heated DESI spray may control desorption kinetics of a target analyte or otherwise control analyte discrimination in detection mode. One embodiment of the DESI spray is heated by heating nebulizing gas that accompanies the electrosprayed solvent. Another embodiment heats a separate gas stream that transports or directs desorbed material to the ion aperture of an analysis instrument. Heating may reduce size of primary droplets, alter the impact dynamics or the energy delivered by the spray to the surface, reduce size of secondary droplets and/or assure desolvation, improve species selectivity or otherwise affect sampling and enhance the ion signal level.

25 Claims, 4 Drawing Sheets

METHOD AND APPARATUS FOR EMBEDDED HEATER FOR DESORPTION AND IONIZATION OF ANALYTES

RELATED APPLICATIONS

This application claims the benefit of the U.S. provisional patent application 61/194,770 filed on Sep. 30, 2008.

FIELD OF INVENTION

The invention generally relates to an ion source apparatus and methods of ionizing and desorbing an analyte sample by Desorption Electrospray Ionization (DESI), the process of creating ions for analysis, directly from sample surfaces by impinging an electrically charged spray onto the surface to produce ions of material desorbed therefrom.

BACKGROUND OF INVENTION

Desorption electrospray ionization (DESI) is a desorption/ionization (DI) technique useful for sampling surface material under ambient conditions. The technology has been described in R. Cooks et al. Science (Mass Spectrometry Sampling Under Ambient Conditions with Desorption Electrospray Ionization, *Science*, 2004, 306, 471-473), and some related technologies are described in a survey article Ambient Mass Spectrometry, *Science,* 2006, 311, 1566-1570, both of which articles are hereby incorporated by reference. In DESI devices, a small jet or atomized solvent stream directed at a target surface, carries charge to the surface and causes desorption of material from the surface into secondary droplets or vapor, which pass to the inlet of a mass spectrometer or similar analysis instrument. DESI devices are commercially available instruments sold by Prosolia of Indianapolis, Ind. The commercial devices can be directed at samples under ambient conditions to produce ionized material ("analyte") from a targeted sample region, and the ions so produced are provided directly to standard mass spectrometer or ion mobility analyzer instrument.

The mechanism of desorption, which may involve charge buildup and/or momentum transfer from the primary spray as well as pressure differential of the stream flowing past the target surface, can affect different targeted substrates and analytes differently. Despite, or partly because of the simplicity of a basic DESI ion source, the instrument has limited spatial resolution and the ion signal may degrade if setup parameters are changed. It is desirable to extend or improve the analytical and operating capabilities of a DESI ion source.

SUMMARY

The present invention advances capability of the prior art by providing a DESI spray that is heated to modify or thermally control the spray for analyte desorption at a target locus on a sample. The heated DESI spray is, in an embodiment, operated to control spot size and enhance spot resolution in an imaging mode. It may also be operated to affect surface energy threshold for desorption or otherwise affect analyte detection, e.g., the nature and signal quality of the desorbed analyte. In alternative embodiments, the DESI spray may be heated by heating the nebulizing gas that accompanies the electrosprayed solvent, by heating the device itself, by heating the liquid provided to the DESI spray assembly, or by a combination of these methods. Heating may be applied at a level to reduce size of primary droplets, to reduce the effective area of the spray impinging on a sample surface, to alter the impact dynamics or increase energy delivered by the spray to the surface or enhance volatilization of a target analyte, to promote specific reactivity of a multicomponent spray with the target, to reduce size of secondary droplets, or otherwise to enhance the ion signal level.

BRIEF DESCRIPTION OF DRAWINGS

These and other features of the invention will be understood from the description herein and illustrative drawings, taken together with the claims appended hereto, wherein FIG. 1 schematically shows a typical DESI system of the prior art directed toward a target surface and the inlet of an ion analyzer;

DETAILED DESCRIPTION

The invention will be best understood following a description of typical DESI probe constructions and operation.

Figure 1:
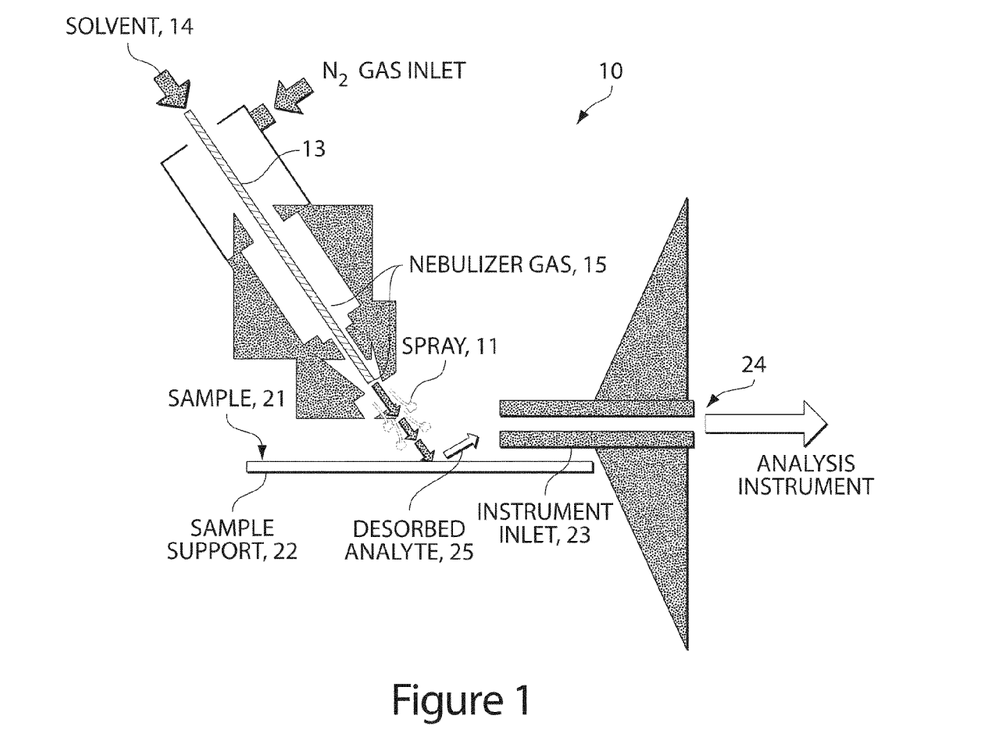

FIG. 1 illustrates schematically a representative prior art DESI ion-sampling probe system 10. In this system a spray 11 may be generated by a conventional electrospray device 12. The device 12 includes a spray capillary 13 through which the liquid solvent 14 is fed. A surrounding nebulizer/gas propellant housing or capillary 15 forms an annular chamber or passage through which a nebulizing gas such as nitrogen ($N_2$) is fed at high velocity. In one example, the liquid solvent is a water/methanol mixture and the gas is nitrogen. A high voltage is applied to the liquid solvent by a power supply via a metal connecting element. The result of the fast flowing nebulizing gas interacting with the liquid leaving the capillary 13 is to form the DESI-active spray 11 as a well-directed, charge-carrying spray comprising liquid droplets. DESI-active spray 11 may also include neutral atmospheric molecules, nebulizing gas, and gaseous ions. Although an electrospray device 12 has been described, any device capable of generating a stream of liquid droplets carried by a nebulizing gas jet may be used to form the DESI-active spray 11. Further, the specific subassembly for imparting charge to the spray may take several alternative forms. These may include applying a voltage potential to a conductive (e.g., stainless steel) capillary 13, providing a high voltage wire extending centrally inside a non-conductive capillary; providing a high potential needle adjacent the spray outlet, or other known charge-imparting arrangements.

The spray 11 is directed onto the sample material 21 which resides on or in the surface material of a substrate 22 to cause analyte to be desorbed from the substrate. Desorbed material 25 leaving the sample is collected and introduced into the atmospheric inlet or instrument interface 23 of a mass spectrometer for analysis, by an ion transfer line 24 which is positioned in sufficiently close proximity to the sample to collect the desorbed ions. Surface 22 may be moveable with respect to device 12, or may be mounted on a moveable platform that can be moved in the x, y or z directions by well known drive means, so as to desorb and ionize sample 21 at different areas of the substrate. This may be carried out to create a map or image of the surface distribution of detected constituents of a sample. Electric potential and temperature of the platform may also be controlled by known means. Any atmospheric interface that is normally found in a mass spectrometer will be suitable for accepting the DESI stream. Good results have been obtained using a typical heated capillary atmospheric interface. Good results also have been obtained using an atmospheric interface that samples via an extended flexible ion transfer line made either of metal or an insulator.

The exact interaction which takes place between the DESI-active spray 11 and the sample 21 to generate the sample ions may involve more than a single ionization mechanism. Several ion formation mechanisms merit particular mention.

One involves the "splashing" of charged nanodroplets from the spray onto the surface during which molecules on the surface are picked up by the impacting droplets. In the DESI experiment, the charged primary droplets produced by the electrospray are pneumatically directed at high velocities (ca. 120 m/s)(30) toward the surface. In general terms, there are two possible outcomes which may result from droplets impinging onto a surface, deposition or splashing, with the latter resulting in secondary droplet formation. In both cases prior droplet impact may have created a liquid film at the surface. The outcome of the impact is governed by the fluid properties (i.e. viscosity and surface tension) and kinematic parameters (i.e. droplet size and velocity), which are described by Reynolds and Weber numbers. Simulations of the DESI process indicate that the desorption event involves dissolution of the solid-phase analyte present at the surface into the deposited liquid film and its subsequent removal by splashing caused by impinging solvent droplets. Subsequently, ionization of analyte in secondary droplets occurs by ordinary solvent evaporation and ion formation mechanisms that apply to the conventional electrospray ionization process (ESI) used to examine bulk solution-phase samples.

A second mechanism may involve charge transfer between a gas phase ion and a molecular species on the surface with enough momentum transfer to cause desorption of the surface ions. Charge transfer can involve electron, proton or other ion exchange. The process, known from studies of ion/surface collision phenomena under vacuum, can be exploited to ionize certain materials such as carotenoids from fruit skin or cholesterol from metal substrates.

A third mechanism is volatilization/desorption of neutral species from the surface followed by gas phase ionization through proton transfer or other ion/molecule reactions. Increased signal intensity of certain highly basic and volatile alkaloids (e.g., coniine or coniceine) when sprayed with a 1 M $NH_3$ solution (compared to signal intensities when using 0.1% acetic acid) support this mechanism. It is believed that in most experiments, more than one mechanism will contribute to the resulting mass spectrum. However, for a given target analyte, the composition of electrosprayed solvent and physical/geometrical characteristics of the surface may be varied to selectively enhance mechanisms responsible for ion formation for optimal signal.

Thus, DESI is carried out by directing pneumatically-assisted electrosprayed microdroplets through the atmosphere at a surface of interest from which the spray picks up surface components such as small organic molecules or large biomolecules, ionizes them, and delivers them, as desolvated ions or electrically charged microdroplets, to an analysis device. Several physical mechanisms are involved. The spray initially forms a thin film of liquid in a spot region of the sample surface, into which a condensed-phase analyte dissolves. This is followed by desorption via momentum and/or energy/charge transfer when additional electrospray droplets collide with the liquid layer, forming dissolved analyte secondary microdroplets or gas phase ions in the surrounding atmosphere. The geometry is arranged to pass these charged analyte-containing secondary microdroplets or ions to the inlet of a mass spectrometer or other ion analyzer. The resulting mass spectra are similar to normal electrospray ionization (ESI) mass spectra.

The DESI analysis instrumentation may be set to act as a probe for detection or characterization of one or more specific substances (such as a product, a contaminant, a biological constituent or a fragment of any of these materials), or may be configured to scan a sample and operate as an imaging device, producing a color coded image representing the chemical makeup of material associated with each point of the sample. When imaging tissue, the image may depict small molecule or endogenous metabolite distribution, and the images may be used to define surgical tumor boundaries, carry out drug uptake studies or perform other structure-based assays or analyses.

The contents of the solvent spray, the gas flow rate, the solvent flow rate, the applied potential, the spray angle and the ion uptake angle, as well as the various distances between, and alignment of, the spray, the sample and the intake to the mass analysis device are all factors that can be varied to optimize the signal levels obtainable for a particular sampling situation. Within these general parameters, the size of the impinging spray on the sample surface strongly affects resolution, and the charged liquid flow affects ion production.

In DESI, the charged droplets initially produced by the spraying process are further accelerated and guided toward the target surface using a high velocity gas stream, which will be generally referred to herein as the nebulizing gas. This gas stream flows in an annular region surrounding the spray. The sprayed liquid, containing a solvent or mixture of solvent and other components, may initially adsorb to a small target region of the surface, or "spot", forming a thin film. As the spray continues and charge builds up, arriving droplets interact with the sample surface so that ions are desorbed or secondary charged droplets pick up the analyte and become entrained in the accompanying gas stream. Subsequently, ions created through the ion desorption and/or charged droplet evaporation processes are introduced into the mass spectrometer via an inlet to the vacuum system. If complete desolvation does not occur due to the set flow rates, droplet size and other conditions of operation, various means known in the art can be employed to improve desolvation of the microdroplets and prevent fouling of the mass spectrometer or other ion analysis device. Such means are commonly present in the sample receiving stage of analyzer instruments.

DESI offers significant advantages over competing technologies for qualitative microanalysis of material because unlike most ion spectrometry technologies, DESI may be operated under ambient conditions on samples with little or no preparation, and DESI is a soft ionization technique that causes minimal fragmentation of the target analytes. It may be operated in a microprobe mode to acquire point samples with high specific sensitivity, or in an imaging mode to develop an image of the sample displaying the localized presence of detected ions. When operated as a probe, it can accept samples that are not even mounted or secured to a stage, and it may interface with special-purpose detectors or software, configured, for example to respond to traces of a specific target such as an explosive or drug (when operated as a security screening device), a bioactive product or contaminant (when configured as a pharmaceutical quality-control sampler) or respond to other analyte or fragment thereof. The technology offers less imaging resolution than vacuum-based highly energetic technologies such as SIMS or MALDI, but has the ability to operate quickly in ambient conditions, and the resolution and sensitivity uniquely support many applications.

Operating under ambient conditions, certain paths of the DESI geometry are preferably kept small and aligned. The spray head should be positioned within a few millimeters of the target, at angle between about 30 and 90 degrees, where the steeper angles may be employed to enhance momentum transfer during droplet impact and favor desorption of larger molecules, while gas phase or volatile molecules may generally be picked up by primary or secondary droplets near the surface. When directly receiving ions and charged droplets entrained in the nebulizer gas stream, the secondary ion collector should be positioned within a few millimeters of the impingement spot and may be typically aligned at a shallow collection angle, although other DESI configurations permit greater flexibility in the ion collection geometry. In particular, relatively geometry-independent generation and sampling of ions may be achieved by providing a surround or housing enclosing the sample (as shown, for example, in published international application WO08/082,603 or as described in the ASMS 2008 poster of Venter et al. *Endogenous metabolites excreted through the skin and analyzed by Geometry Independent Desorption Electrospray Ionization*) and/or by providing an auxiliary gas stream, with or without such enclosure, to direct or carry ions to the analysis instrument (as discussed further in relation to FIG. 3, below).

Generally, signal intensities achieved for the analyte ions depend on several factors, including the volumetric flow rate of the liquid solvent, solvent composition and the nebulizing gas pressure and/or gas flow rate of the DESI spray head. An increase in the solvent flow rate may cause a concomitant increase in the spot size on the target, resulting in overall greater emission of ion-bearing analyte-charged droplets from a larger region of the surface; the greater flow may also affect the size of both the primary spray droplets and the secondary droplets containing the desorbed analytes. In general the secondary droplets are quite small, so the solvent substantially evaporates leaving the charge residue on the entrained material which enters the mass spectrometer as ions.

The larger spot size of the primary charge droplet beam caused by increased solvent flow reduces spatial resolution when operated in an imaging mode, and may also increase spatial cross-contamination of the analyte with material from a surrounding region of the surface.

While lower flow rates will decrease the spot size and thus may offer enhanced spatial resolution, in practice this may reduce the yield of secondary analyte-bearing microdroplets, and result in a concomitant loss in the ion signal level. Thus there is a trade-off between sampling resolution and sampling signal level. This trade-off between spatial resolution and signal intensity is also an inherent limitation of SIMS and MALDI ion imaging systems. Several workers have proposed enhancements of the basic DESI configuration, for example by a mechanism such as directing a laser at the spot, to selectively increase the energy level and enhance ion desorption in a smaller spot and thus enhance the signal as well as the spatial resolution. However, such higher-energy variations, while of great value for investigations requiring high resolution, such as histological imaging, require more complex device structure and alignment of the additional energy beam subsystem, imposing constraints on sample preparation or staging, or potentially affecting the composition of, or causing degradation or fragmentation of, the analyte.

The invention will be understood with reference to the overall structure of a DESI ion source, as shown, for example in FIG. 1 of U.S. Pat. No. 7,335,897 or corresponding PCT international publication WO2005/094389, the entire specification and disclosure of which are hereby incorporated herein by reference. In general terms, the present invention comprises an improved DESI ion spray which is heated, providing enhanced production of ions; the heating may enhance spatial resolution (spot size) of the spray, or provide selectivity as to the mass, chemical type or other characteristic of the desorbed analyte. The DESI ion-sampling source is heated to a temperature above that of the conventional ambient temperature, to between about 30° C. and about 600° C., and preferably to between 50° C. and 300° C. The temperature may be a level that reduces spot size on the target, or a level that increases temperature of the desorption spot on the target, or both. When the DESI spray comprises several components each intended to meet a specific requirement (such as liquid droplet momentum transfer, vaporizable solvent having functionality for interaction with the desorbed analyte ions, or chemical reactant for surface interaction with a target fragment), the temperature may be selected to optimize the ratio of components at the surface.

In one embodiment a heater is incorporated in the DESI instrumentation to heat nebulizing gas provided to the assembly. The gas may flow coaxially with the feed capillary to the DESI spray nozzle, or may enter coaxially via an annular opening around the liquid spray. In an alternative or additional embodiment, an embedded heater may heat the solvent which flows to the DESI emitter. However, owing to the generally low boiling points and small flux of solvent, relatively little heat may be supplied in the liquid and the spray mechanics would vary widely with liquid temperature, so heating of the gas is preferred for solvents having a low boiling point. In another embodiment, a heated second gas flow is introduced over the target sampling region to direct desorbed analyte toward the analyzer inlet, which can be positioned to receive a cross-flow, for example at 90 degrees to the normal of the target surface.

The DESI heating in accordance with the present invention can affect several of the underlying physical mechanisms of ion production, and as such can be effective to enhance control over a number of DESI spray parameters:

1. reduction of spot size of the incident primary charged droplets on the target without necessitating a reduction in liquid flow thereby improving the achievable spatial resolution for surface imaging;
2. partial desolvation of the incident primary droplets before impacting the sample;
3. desolvation of the secondary droplets exiting the surface, which bear the analyte of interest, prior to entering the ion analyzer;

4. reduction of surface contamination otherwise caused by redistribution of analyte molecules in the adsorbed solvent/reactant spot at the surface; and
5. enhanced desorption via thermal effect (solvation, reaction, volatilization or other energy-dependent desorption kinetics).

Combinations of the foregoing effects provide improvements of the DESI source as a probe or imaging device, and enable new control modalities for discrimination of the mass, chemical functionality or other properties of targeted analytes.

Existing mechanisms of DESI desorption and ion generation include mechanisms whereby incident droplets pick up proteins and large molecules upon surface impact and impart charge to create corresponding ions as the solvent evaporates, and mechanisms whereby gas phase solvent ions protonate or otherwise react with analyte molecules on the surface to generate ions from materials having low desorption energies, including volatile or semi-volatile compounds, low-polarity molecules of smaller size, low molecular weight polar compounds and certain inorganic ions. The heater of the present invention allows a further tailoring of the incident droplet size/momentum conditions, of the spot temperature desorption threshold conditions, and of the resulting secondary spray composition at the desorption surface. In addition the heated gas stream extends the operating range to allow a high-volume, high-charge spray to form a large surface spot, or interrogate a surface region, while still effectively desolvating the secondary droplets for screening applications such as drug or explosives detection.

FIG. 1 schematically illustrates a typical prior art DESI ion sampling device. Reference is made to the above-mentioned U.S. Pat. No. 7,335,897 for a description of its operation and representative operating conditions. By way of example and without implying any limitation, the DESI spray device may operate with a spray fluid such as a water/alcohol mixture, at a potential of 1-5 kV, at a feed rate of about 1-3 µL/min with a nebulizer gas flow of nitrogen or other gas at 5-10 atmospheres. An ultrasonic nozzle or piezo-driven liquid flow mechanism may be actuated to assure that the primary spray droplets are of uniform and small size (under about 5 µm), and the nebulizer gas may serve to transport, rather than to generate the primary spray.

Figure 2A:
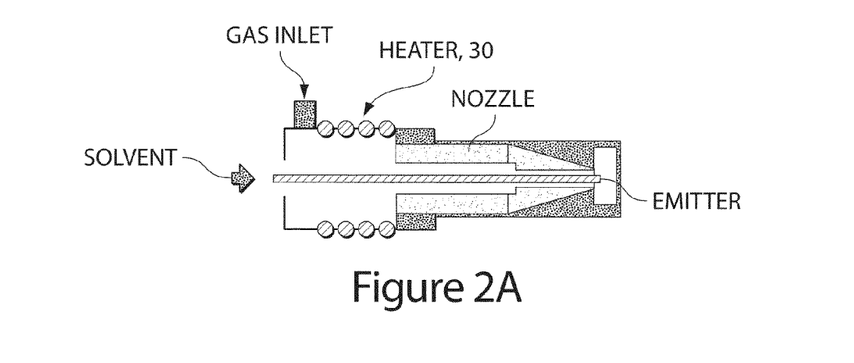
FIG. 2A is a cross-sectional view of an embodiment of the invention having an embedded heater in the nozzle of a DESI ion source.

FIG. 2A shows one embodiment of the invention wherein a heating element 30 is provided in the body of a DESI spray assembly to elevate the temperature above ambient. The spray assembly includes a nebulizer gas feed portion surrounding a liquid feed, and the heater is arranged to heat the flow of nebulizing gas. In practice, owing to the small dimensions of the feed tube, and the relatively small and slow mass flow of liquid, some heat may be transferred also to the spray liquid both from the surrounding gas and from the solid body of the spray assembly. FIG. 2A is intended to be schematic, and the actual structure of the heater and the gas-channeling body may be implemented differently, for example with the gas flowing through multiple passages in a heated metal block of large and stable thermal mass. The heater may be controlled in response to sensing elements (not shown) so that the gas dependably reaches a desired or set temperature as it passes to the spray tip. Similarly, the dimensions and relative sizes of the gas passage and the liquid supply capillary are schematic only, and may be varied. It is preferred that the construction allow the liquid temperature to remain substantially unaffected by the heater and the heated gas, despite the relatively small dimensions and short thermal conduction paths presented by the structure of the ion source device.

Figure 2B:
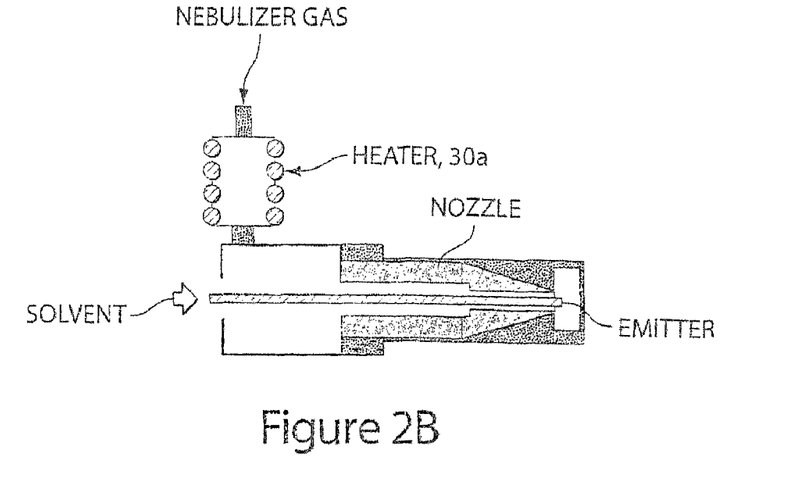
FIG. 2B is a cross-sectional view of an alternative or additional embodiment of the invention with heating elements arranged for external heating of the nebulizing gas supplied to the DESI spray nozzle.

FIG. 2B shows another embodiment of the present invention, wherein a heater 30a is positioned about a gas inlet ahead of a DESI spray assembly. In this embodiment, the heater heats the nebulizing gas being fed to the spray assembly. In other respects, the assembly is similar to that of FIG. 2A; the heated gas may be arranged to transfer heat to the liquid capillary as it passes through a preliminary chamber, or may be configured to maintain thermal isolation of the liquid and the gas streams before the liquid and gas both exit at the tip of the spray nozzle.

In general, the spray assembly atomizes the charged liquid at a rate typically of a few microliters/minute, and the dimensions of the capillary and surrounding nozzle body as used in the prior art correspond to such operation. In operation, one configuration for DESI operation may position the DESI spray 1-5 mm from the target surface at an incidence angle between about 30° and 90°, and a vacuum uptake tube or ion sampling aperture for the mass spectrometer will be positioned to catch the ions desorbed from the spot so formed. In other configurations, the DESI spray axis and ion uptake may be positioned at 90° or at 180° to each other.

Figure 3:
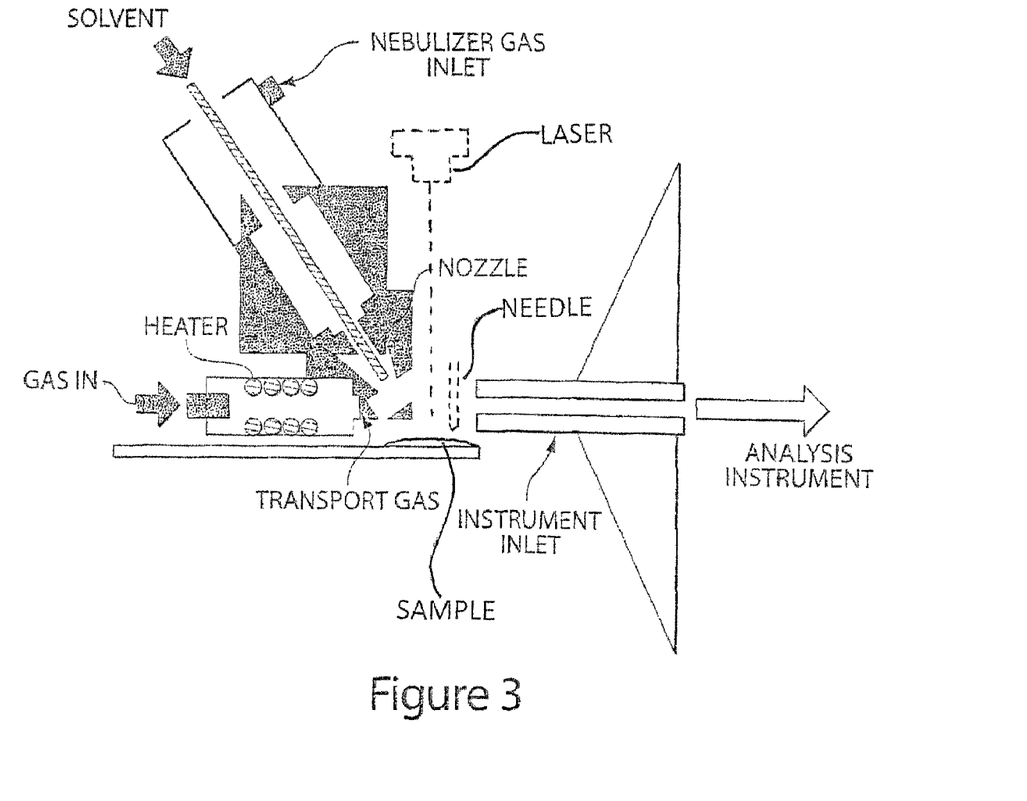
FIG. 3 shows a DESI embodiment having a heated second gas flow directed toward the ion inlet in the path of the incident and secondary droplets to direct the scattered secondary droplets into the ion inlet and to also aid in desolvation for improved signal level.

FIG. 3 shows an embodiment of the invention having a second gas flow, distinct from the nebulizing gas stream. The second stream is heated and is positioned and directed over the target surface toward the ion analyzer to carry ions desorbed from the surface toward the ion sampling aperture. In this embodiment, the heated flow may provide thermal energy to the target surface, and also aid in desolvation of secondary droplets for improved signal level. A needle may extend proximate to the target surface and be maintained at a high potential to draw ions from the surface into the heated transport stream. In that case, a neutral spray liquid may be used for the primary spray, i.e., the primary spray liquid need not be charged.

The ion source of FIG. 3 in certain embodiments is constructed as a hand-held probe, such that the atomized spray is directed toward a spot in a well-determined sampling region that is defined, for example by a fixed front contact surface of the probe, and a separate flow of heated air is directed across the sampling region to carry desorbed ions to the inlet of the analysis device. The tip of the probe in one such embodiment possesses a surrounding shell or cup (not shown) that effectively forms an enclosure about the sampling region, the spray and the ion inlet when urged against a target surface. The device in related embodiments also incorporates a controller and suitable control valves, which operate, for example to turn on the second gas flow after a short delay to permit analyte solvation and desorption while minimizing the amount of transport gas provided to the ion aperture. Limitation of the gas volume in alternate embodiments is achieved by controlling the flow of transport gas to be intermittent rather than continuous, or by varying the flow rate differently as needed to effect surface heating, desolvation and transport.

Figure 4:
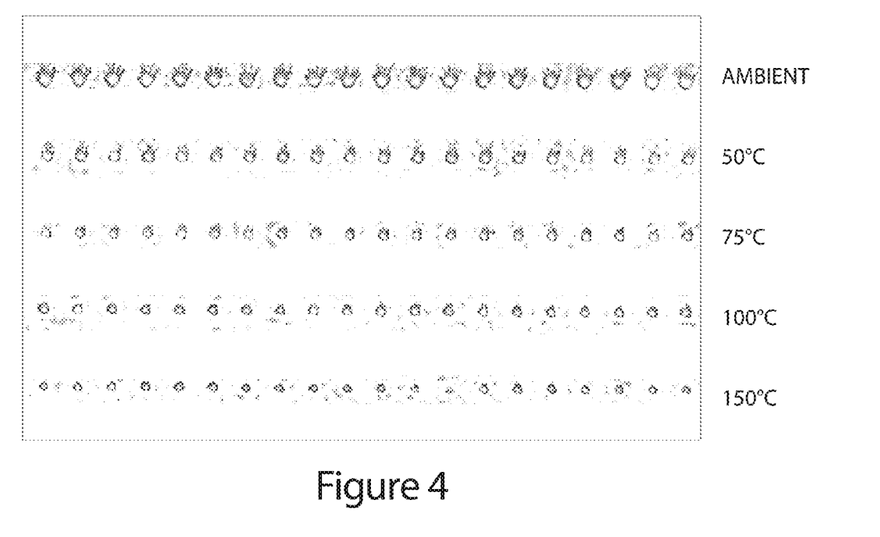
FIG. 4 shows DESI spot sizes as a function of temperature under standard operating conditions, illustrating the reduction in the spot size of the incident primary charged droplets with temperature at a constant flow rate, thereby improving the achievable spatial resolution for surface imaging.

FIG. 4 shows the spot sizes which occur at a target surface under standard operating conditions as a function of temperature of the nebulizer gas stream. By standard conditions are understood the typical DESI volumetric spray rate, target distance and incidence angle that produce good signal levels with a prior art (not heated) DESI spray from a typical target. FIG. 4 shows the spot size on the target for a given set of spray parameters, and the spot sizes produced at various elevated temperatures. The top row shows spots deposited following conventional DESI under ambient temperature (room temperature, circa 25° C.). The second and subsequent rows show spots developed following DESI at the same liquid flow rate and target distance, but with nebulizer gas delivered to the spray head through a heater maintained at a temperature of 50° C., 75° C., 100° C. and 150° C., respectively. As shown, progressively increasing the temperature causes the spot size to drop to less than about 20% of the initial spot size, from 250 µm to less than about 50 µm, while the primary spray continues to carry the same charge and generate ions. Heating thus provides a substantial improvement in spatial resolution while maintaining the quality of the ion signal. Concomitantly, ions are desorbed from a smaller area, reducing the potential for cross-contamination if the analyte is distributed non-uniformly. The spot sizes of FIG. 4 represent proof of principal verification for one prior art DESI spray mechanism; however, in other embodiments a DESI spray may target a larger area and the heated spray of the present invention can permit sampling from a region of several mm$^2$ or up to ten cm$^2$, thus extending the size of the sampling region while maintaining a good ion signal.

Figure 5:
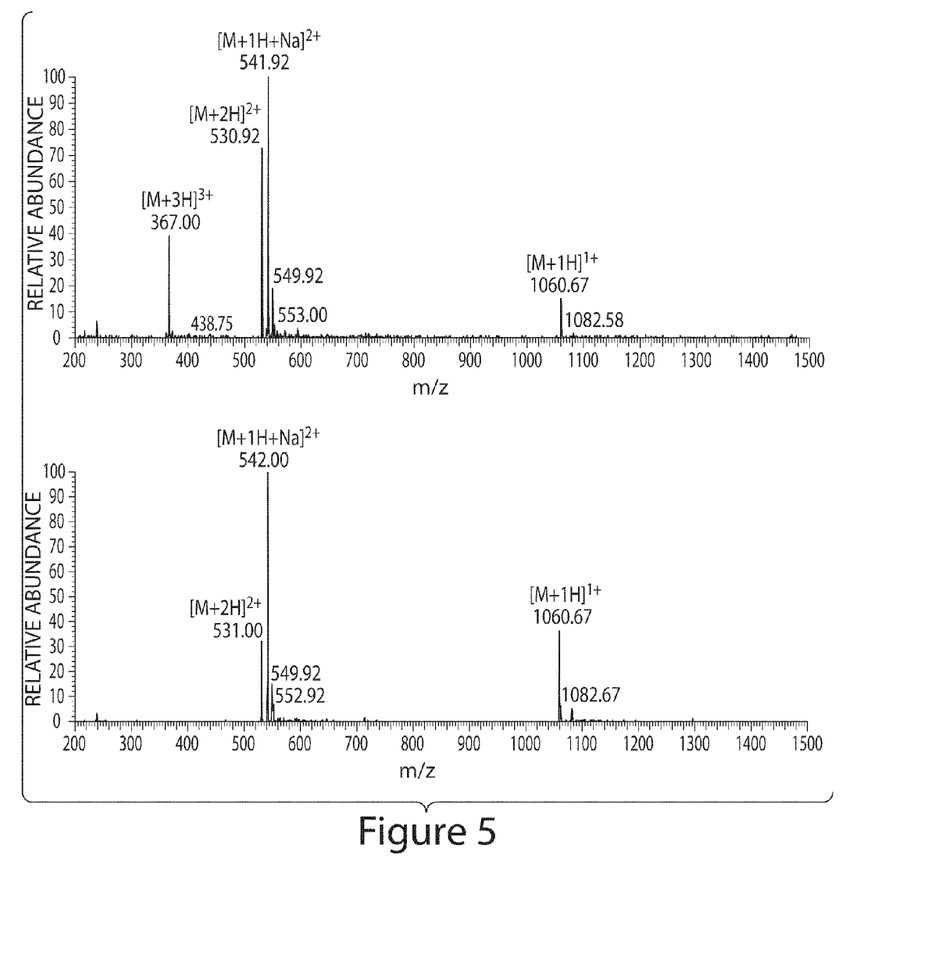
FIG. 5 (Top) shows a DESI-sampled mass spectrum of 3 ng/mm$^2$ bradykinin (RPPGFSPFR) under standard DESI conditions. (Bottom) shows the corresponding mass spectrum of 3 ng/mm$^2$ bradykinin (RPPGFSPFR) using a heated DESI source at a temperature of 100° C.

FIG. 5 shows a comparison of DESI mass spectra recorded of 3 ng/mm$^2$ of bradykinin peptide using an ion trap mass spectrometer. The top panel shows a typical DESI mass spectrum of the peptide recorded using standard DESI conditions. The bottom shows the DESI mass spectrum of the peptide recorded using a heated DESI source with the temperature set at 100 C. FIG. 5 illustrates the effect of heating the nebulizing gas which in this case results in a reduction of the charge states represented in the secondary stream, producing relatively more abundant ions in lower charge states. As seen in the bottom panel of FIG. 5, the triply-charged ion of bradykinin peptide is completely absent from the heated DESI sample, while singly-charged ions are more abundant, in comparison to the top panel.

In addition to the enhanced resolution, certain desorption mechanisms affected by the heated spray may be exploited by various methods to enhance analysis for specific analytes or target substrates. Thus, for example, the heated nebulizer gas may be initially turned on to precondition or elevate the temperature of the surface, before commencing the solvent electrospray, potentially aiding desorption of analyte materials (e.g., enhancing desorption of heavier analytes) or promoting desolvation of ions and secondary droplets, or altering the molecular weight distribution or solubility characteristics of material desorbed from the surface. Rather than seeking to enhance image resolution with smaller spot sizes, the spray may be operated to enhance the signal while maintaining the same spot size generally in the range of 50-250 µm. The device can also be operated at a higher liquid flow rate to carry increased charge and span a large region for operation as a screening probe. In this case, the heated gas may assure that the droplet interaction at the surface still produces a strong desorbed ion flow to the analyzer. Thus, for example, it can assure that the primary droplets do not become too large, and that the delivered charge density and the interaction kinetics at the surface remain favorable for desorption, and that the secondary droplets are quickly desolvated despite the greater feed rate and area of interrogation, passing to the ion analyzer aperture. Further, while the spray generally forms a spot size at the surface that increases with distance from the probe to the surface and with an elliptic spread dependent upon incidence angle, the heater allows greater flexibility to maintain an optimal primary droplet beam flux and shape such that analytes are desorbed from a spot under 50 µms, or a selected size between 50-250 µm, or simply to enhance desolvation of the secondary charged droplets. The heater also enables one to use a very large nozzle to produce larger spots or interrogate a surface region requiring correspondingly high solvent flow rates, without degrading performance.

Thermal control, by providing an embedded heater, or heating the solvent, the nebulizing gas and/or an auxiliary transport gas, thus allows one to tune or optimize the ion desorption process to selectively enhance an analyte signal of interest on a target substrate. The invention thus being disclosed and illustrative embodiments thereof described, variations and modifications will be understood by those skilled in the art, and such modifications are considered to be within the scope of the invention defined by the claims appended hereto.

What is claimed is:

1. A method for desorbing and ionizing an analyte from a sample to provide ions to a spectrometer or analyzer, wherein the method comprises directing a spray of liquid droplets at a surface of the sample to interact with the surface in a region of the sample, and applying charge to at least one of the liquid or the surface such that analyte is desorbed from the surface forming a stream of analyte ions for analysis, and wherein the spray of liquid droplets is thermally-controlled.

2. The method according to claim 1 in which the spray is heated above ambient by one or more steps selected from among
    heating a nebulizing gas;
    heating a sprayer assembly; and
    heating an auxiliary gas stream.

3. The method according to claim 2 wherein the heated spray contacts the sample material under substantially atmospheric pressure.

4. The method according to claim 3 wherein the spray is heated to a level effective to achieve one or more of
    reducing spot size on the surface of the sample and thereby limit cross-contamination of desorbed material;
    controlling size and/or energy of primary and/or secondary droplets; and
    reducing the amount of spray liquid impacting the surface while increasing charge transported for enhancing ion formation.

5. The method according to claim 1 implemented in a device that, in addition to thermal control, controls one or more of
    liquid pressure, and
    angle and distance to sample from a spray nozzle, so as to optimize signal strength of desorbed ions passed to a mass spectrometer.

6. The method according to claim 1 wherein the spray is generated from a liquid and a nebulizing gas, wherein one or both of the liquid and the gas are heated.

7. The method according to claim 6 wherein the sample is a biological material and the liquid comprises a biochemical reagent that reacts with the biological material to form desorbed analyte ions of the reaction, or wherein ions are introduced into the liquid to interact with the sample material and generate desorbed ions of complexes between the sample material and the ions.

8. The method according to claim 1 wherein the temperature of the spray is controlled by supplying a heated gas stream, wherein the heated gas stream is a nebulizing stream surrounding a spray nozzle and effective to at least partially evaporate primary droplets and thereby control desorption at the target surface, or is a transport gas stream positioned to transport analyte desorbed from the surface toward an ion aperture of an analyzer.

9. The method according to claim 8 wherein the heated gas stream is a nebulizing stream that reduces spot size at the surface while providing a charge/volume ratio for an effective ion signal level of material desorbed from the surface.

10. The method according to claim 1 in which the liquid includes one or more of
    a solvent for an analyte of interest in the sample,
    an ionization promoter, and a reagent for generating desorbed ions produced from a reaction between the sample material and the reagent.

11. The method according to claim 1 in which the spray is configured to spray a spot on the sample and the spot is scanned with respect to the sample to provide desorbed ions representing different parts of the sample, or a chemical content image of the sample.

12. The method according to claim 11 in which the spot is configured by masking to sharpen resolution.

13. The method according to claim 11 in which the spot is configured by spraying mobilized droplets of the liquid toward the surface of the sample material and droplets are charged by applying an electric potential via a needle electrode at the location of the spot.

14. The method according to claim 11 in which the spot is configured by directing the spray to the surface of the sample material with an energy level just below a level needed for desorption and ionization of the analyte in the sample material, and heating adds sufficient energy at the spot to cross the desorption threshold for an intended or target analyte.

15. The method according to claim 14 in which further energy is supplied by a laser.

16. The method according to claim 14 wherein the temperature is controlled to adjust the energy level.

17. The method according to claim 1 in which in the sample is, or is supported on,
a solid or thin film surface,
a glass slide or stage,
a liquid,
frozen material,
a free-standing object, or
in vivo material.

18. A method for ionization and desorbing an analyte in a sample as in claim 1 or 11 in which one or more samples are bound to a sample slide by one or more ligands, receptors, lectins, antibodies, binding partners, and chelates.

19. A system for analyzing a sample material comprising: apparatus for generating and directing onto the surface of the sample a heated spray to interact with the surface and generate ions of analytes desorbed from the sample, the system being arranged to provide a stream of ions of analyte desorbed from the surface to an ion inlet aperture of an analyzer and wherein the system includes a heater to enhance ion signal quality.

20. The system according to claim 19 in which the analyzer is selected from among a group of analyzers which include a TOF mass spectrometer, quadrupole, orbitrap, Wein filter, sector, IMS, ion trap mass spectrometer or other ion analyzer.

21. The system according to claim 19 in which the apparatus for generating a spray includes a heated electrospray device.

22. The system according to claim 21 wherein a heating element
is located along and surrounding a nebulizing gas passage, or
heats a gas flow arranged to direct matter desorbed by the spray toward the inlet aperture of an ion analyzer.

23. Apparatus for analyzing an analyte situated on a substrate comprising: a heated spray source directable toward the substrate; and an analyzer with an intake aperture operable to collect desorbed ionic products of the analyte generated by the spray.

24. The apparatus according to claim 23 wherein the heated spray is heated by a cross flow of heated gas separate from a nebulizing gas and configured to transport desorbed ions to the intake aperture.

25. The apparatus of claim 24, wherein said spray is carried out in an enclosure and the cross flow of heated gas flows intermittently to limit pressure or quantity of said gas.

* * * * *